(12) United States Patent
Kenmochi et al.

(10) Patent No.: US 7,833,207 B2
(45) Date of Patent: Nov. 16, 2010

(54) PANTS-TYPE WEARING ARTICLE

(75) Inventors: Yasuhiko Kenmochi, Kagawa-ken (JP);
Akiyoshi Kinoshita, Kagawa-ken (JP);
Natsuko Aoyagi, Kagawa-ken (JP);
Kayoko Tanaka, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 684 days.

(21) Appl. No.: 11/763,507

(22) Filed: Jun. 15, 2007

(65) Prior Publication Data

US 2008/0009816 A1    Jan. 10, 2008

(30) Foreign Application Priority Data

Jul. 6, 2006    (JP) .............................. 2006-187165

(51) Int. Cl.
*A61F 13/20* (2006.01)

(52) U.S. Cl. ............................ 604/385.01; 604/385.03; 604/385.04; 604/385.25; 604/385.11; 604/385.29; 604/385.3; 604/389; 604/391

(58) Field of Classification Search ............ 604/385.01, 604/385.03, 385.04, 385.25, 385.11, 385.29, 604/385.3, 389, 391
See application file for complete search history.

(56) References Cited

U.S. PATENT DOCUMENTS

| | | | | |
|---|---|---|---|---|
| 4,578,072 A | * | 3/1986 | Lancaster | 604/385.24 |
| 4,670,012 A | * | 6/1987 | Johnson | 604/390 |
| 5,304,162 A | * | 4/1994 | Kuen | 604/391 |
| 5,591,521 A | * | 1/1997 | Arakawa et al. | 428/352 |
| 6,409,858 B1 | | 6/2002 | Popp et al. | |
| 6,524,294 B1 | * | 2/2003 | Hilston et al. | 604/386 |
| 6,579,275 B1 | * | 6/2003 | Pozniak et al. | 604/390 |
| 7,640,638 B2 | * | 1/2010 | Kenmochi et al. | 24/442 |
| 2002/0111596 A1 | * | 8/2002 | Fletcher et al. | 604/385.03 |
| 2003/0135184 A1 | | 7/2003 | Van Gompel et al. | |
| 2005/0113793 A1 | | 5/2005 | Bianco | |
| 2005/0277905 A1 | * | 12/2005 | Pedersen et al. | 604/389 |
| 2008/0016656 A1 | * | 1/2008 | Kenmochi et al. | 24/306 |

FOREIGN PATENT DOCUMENTS

| | | |
|---|---|---|
| EP | 1 523 968 A1 | 4/2005 |
| JP | 2006-175007 A | 7/2006 |
| WO | 2006/033350 A | 3/2006 |

* cited by examiner

*Primary Examiner*—Tatyana Zalukaeva
*Assistant Examiner*—Ginger T Chapman
(74) *Attorney, Agent, or Firm*—Lowe, Hauptman, Ham & Berner, LLP (57) ABSTRACT

A pants-type wearing article includes front and rear waist regions connected to each other by a fastener member in a detachable and refastenable manner. Each of the fastener member includes a sheet-like supporting element adapted to be folded in a Z-shape or an inverted Z-shape as the front and rear waist regions are put flat together and a fastener element. The supporting element has a top section, a bottom section and an intermediate section connecting the top and bottom sections. Between opposed surfaces of the bottom section and the intermediate section, a sheet-like liner section is provided so as to extend from a bottom section's openable end of the bottom section along these opposed surfaces toward a top section's joint end.

19 Claims, 7 Drawing Sheets

PANTS-TYPE WEARING ARTICLE

RELATED APPLICATIONS

The present application is based on, and claims priority from, Japanese Application Number 2006-187165, filed Jul. 6, 2006, the disclosure of which is hereby incorporated by reference herein in its entirety.

BACKGROUND OF THE INVENTION

The present invention relates generally to pants-type wearing articles such as disposable pants-type diapers and training pants and particularly to such wearing articles having front and rear waist regions fastened together by means of detachable and refastenable means.

There have already been proposed various wearing articles of pants-type each having front and rear waist regions fastened together by means of detachable and refastenable fastener means. For example, Publication of EP 1 523 968 A1 (REFERENCE) discloses fastener means used for such wearing article. According to the disclosure thereof, a sheet strip is folded in a Z-shape and an inverted Z-shape and a top section of Z-shape is permanently bonded to an inner surface of one of the front and rear waist regions and a loop element of a mechanical fastener is attached to a bottom section of Z-shape so that the loop element is engaged with a hook element attached to an inner surface of the other waist region. The top section and the bottom section are connected by an intermediate section. The top section and the intermediate section respectively have surfaces opposed to and permanently bonded to each other.

The fastener means used in the known wearing article as has been described above is attached to an inner surface of the wearing article and necessarily it is preferred to use a soft and comfortable material for the sheet strip. On the other hand, it is inevitable that a tension in a circumferential direction is exerted on the fastener means as the sheet strip folded in a Z-shape is unfolded so that the bottom section and the intermediate section are developed in a straight line when the wearing article is actually put on the wearer's body. Such tension is exerted primarily on a starting point of a bonding zone between the top section and the intermediate section. Thus a sufficiently high strength against such tension is required for the intermediate section. However, the inventors have found that it is not easy to obtain the sheet strip which provides for such high strength and simultaneously provides for a soft and comfortable touch since sheet materials providing the soft and comfortable touch often has not a high strength.

SUMMARY OF THE INVENTION

In view of the problem as has been described above, it is an object of the present invention to improve the fastener means for the pants-type wearing article so that a soft and comfortable sheet material can be used for the faster means without anxiety that the fastener means might be easily broken.

The object set forth above is achieved, according to the present invention, by an improvement in a pants-type wearing article comprising a first waist region corresponding to one of front and rear waist regions, a second waist region corresponding to the other of the front and rear waist regions and fastener means fastening the first and second waist regions together in a detachable and refastenable manner along transversely opposite edges thereof so that, in a state of the first and second waist regions put flat together, the fastener means respectively has, as viewed in a circumferential direction, a Z-shape cross-section and an inverted Z-shape cross-section being symmetrical to each other about a center line bisecting a width of the first and second waist regions.

The improvement according to the present invention is in features as follows: the fastener means comprises a sheet-like supporting element folded in a Z-shape or an inverted Z-shape and a fastener element attached to the supporting element, the supporting element having a top section and a bottom section extending in parallel to each other and an intermediate section being contiguous at one end to an end of the top section and at the other end to an end of the bottom section, the top section having a top section's joint end being contiguous to the intermediate section and a top section's openable end opposed to the joint end, the bottom section having a bottom section's joint end being contiguous to the intermediate section and a bottom section's openable end opposed to the joint end, and the top section is permanently attached to an inner surface of the first waist region while the bottom section is attached to the second waist region by means of the fastener means in a detachable and refastenable manner. The supporting element includes a sheet-like liner section extending from a vicinity of the bottom section's openable end along the bottom section and the intermediate section toward the top section joint end so as to cover the bottom section and the intermediate section wherein the liner section is bonded to said bottom section and the intermediate section in a first bonding zone extending between the bottom section's openable end and the top section's joint end. The top section is bonded to one of the intermediate section and the liner section in the intermediate section in a second bonding zone.

In a height direction of the Z-shape and the inverted Z-shape, the first bonding zone and the second bonding zone overlap each other.

According to one preferred embodiment of the invention, the first bonding zone and the second bonding zone overlap each other between the top section's joint end and the bottom section's joint end by a dimension of at least 3 mm.

According to another preferred embodiment of the invention, the fastener means is selected from the group consisting of a pressure-sensitive adhesive, a hook element constituting a mechanical fastener and a loop element constituting a mechanical fastener and the second waist region is provided on an inner surface thereof with the element of the fastener means detachably engaged with the other element of the fastener means.

According to still another preferred embodiment of the invention, the supporting element is formed from a nonwoven fabric made of thermoplastic synthetic fibers having a fineness in a range of 1 to 5 dtex and having a basis weight in a range of 10 to 70 g/m$^2$.

According to yet another preferred embodiment of the invention, the top section and one of the intermediate section and the liner section in the intermediate section have not the second bonding zone in a vicinity of the top section's joint end and therefore are spaced from each other.

According to further another preferred embodiment of the invention, the bottom section and the liner section have not the first bonding zone in a vicinity of the bottom section's openable end and therefore are spaced from each other.

According to an alternatively preferred embodiment of the invention, the liner section is formed by folding back the supporting element along the bottom section's openable end.

According to an additional preferred embodiment of the invention, the liner section is formed from a sheet material provided separately of the supporting element.

According to further additional preferred embodiment of the invention, one of the first bonding zone and the second bonding zone is formed by sealing the thermoplastic synthetic fibers contained in the supporting element and the liner section.

In the case of the pants-type wearing article according to the present invention, the bottom section and the intermediate section of the supporting element folded in a Z- or an inverted Z-shape are unfolded and developed so as to be generally straightened as the article is put on the wearer's body. The bottom section and the intermediate section are provided with the liner section bonded thereto by means of the first bonding zone which, in turn, overlaps the second bonding zone attached to both the top section and the intermediate section or to the sub-section of the liner section extending along the intermediate section with interposition of the intermediate section or the sub-section of the liner section extending along the intermediate section. With such unique arrangement, the material of soft and comfortable touch such as nonwoven fabrics can be used as the sheet-like supporting element without anxiety that the supporting element might be easily broken under the tension of the circumferential direction exerted on the bottom section and the intermediate section unfolded and developed as the article is put on the wearer's body.

Various embodiments of the present invention and effects obtained from these various embodiments will be understood from the detailed description given hereunder in details.

DETAILED DESCRIPTION OF THE PREFERRED EMBODIMENTS

Details of the pants-type wearing article according to the present invention will be more fully understood from the description given hereunder with reference to the accompanying drawings.

Figure 1:
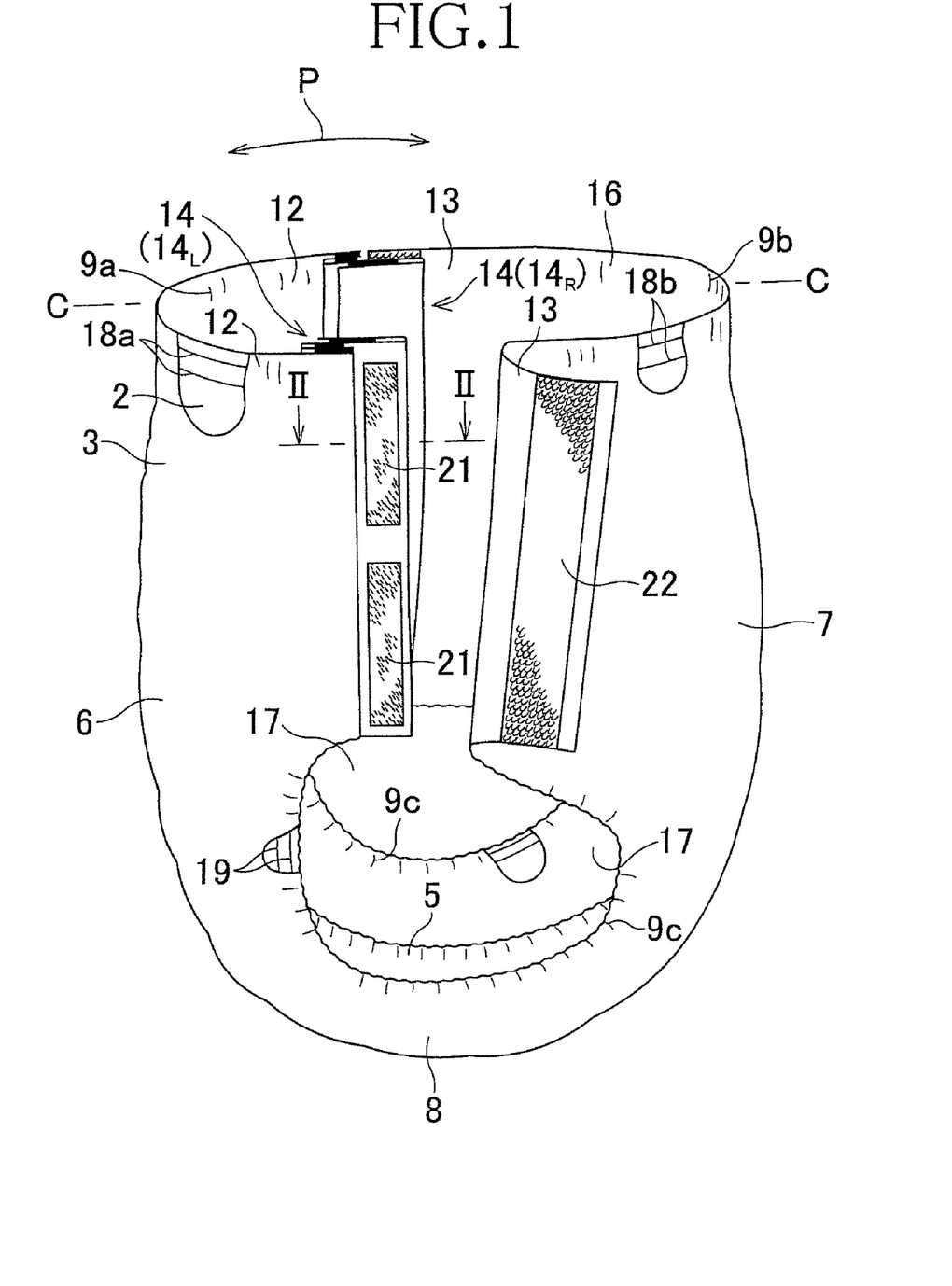
FIG. 1 is a partially cutaway perspective view of a disposable diaper.

FIG. 1 is a partially cutaway perspective view of a pants-type disposable diaper 1 as a typical embodiment of the pants-type wearing article. The diaper 1 has a front waist region 6, a rear waist region 7 and a crotch region 8 extending between these two waist regions 6, 7 wherein these regions 6, 7, 8 are defined by an inner sheet 2 and an outer sheet 3 placed upon each other. The inner sheet 2 is provided on a lower surface thereof with a body fluid absorbent element 5. The front and rear waist regions 6, 7 are detachably connected together along transversely opposite edges 12, 12 of the former and transversely opposite edges 13, 13 of the latter by the intermediary of left side fastener means $14_L$ and right side fastener means $14_R$. Thereupon the diaper 1 is formed with a waist-opening 16 and a pair of leg-openings 17 wherein, along a periphery of said waist-opening 16, a front waist elastic element 18a and a rear waist elastic element 18b are attached in a stretched state to the inner sheet 2 and/or the outer sheet 3. Along peripheries of the respective leg-openings 17, leg-surrounding elastic elements 19 are attached in a stretched state to the inner sheet 2 and/or the outer sheet 3. The fastener means $14_L$, $14_R$ are symmetric to each other about a center line C-C bisecting a width of the diaper 1 as will be described with reference to FIG. 4 (See FIG. 5 also) and attached to an inner surface of the transversely opposite edges 12, 12 of the front waist region 6. Each of these fastener means $14_L$, $14_R$ includes a hook element 21 constituting the so-called mechanical fastener. A loop element 22 adapted to cooperate with the fastener element on the front waist region 6, i.e., the hook element 21 is attached to each of the transversely opposite edges 13 of the rear waist region 7. In this way, the edges 12, 12 and the edges 13, 13 can be disconnected one from another and reconnected one to another. It should be noted that FIG. 1 shows the diaper 1 having gathers 9a, 9b, 9c around the waist-opening 16 and the leg-openings 17 formed under contraction of the waist surrounding elastic elements 18a, 18b and the leg-surrounding elastic elements 19.

Figure 2:
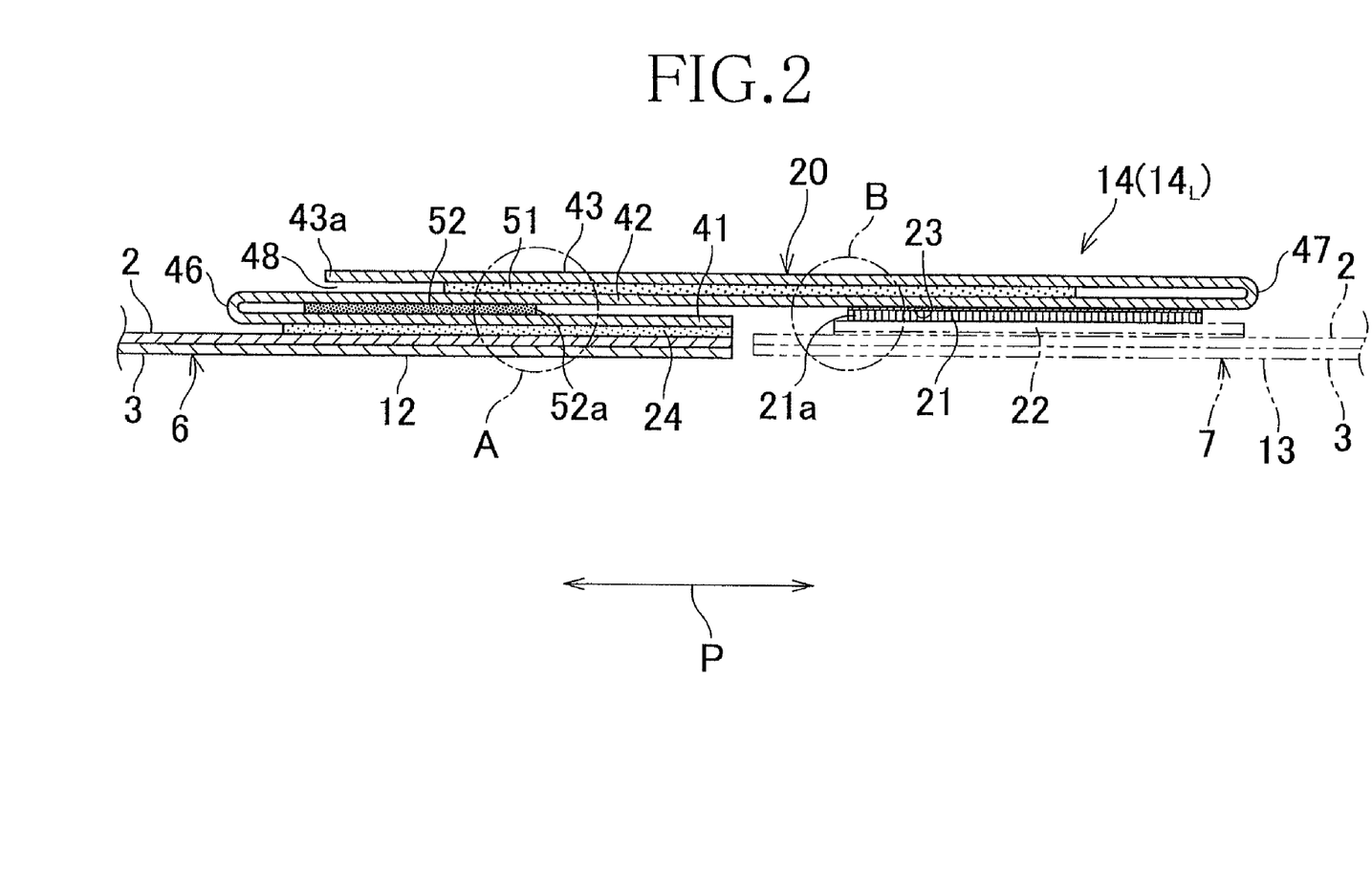
FIG. 2 is a sectional view taken along the line II-II in FIG. 1.

FIG. 2 is a sectional view taken along the line II-II in FIG. 1, in which the side edge 13 of the rear waist region 7 and the loop element 22 are indicated by imaginary lines and the loop element 22 is shown in engagement with the hook element 21. Referring to FIG. 1, the inner sheet 2 and the outer sheet 3 are bonded to each other by use of appropriate adhesives or sealing techniques. The fastener means $14_L$ comprises a sheet-like supporting element 20 and the hook element 21 attached to the supporting element 20 using bonding means 23 such as adhesives. The supporting means 20 has a first section 41 permanently bonded to the inner surface of the front waist region 6 by means of an adhesive layer 24, a second section 42 being contiguous to the first section 41 so as to extend from the front waist region 6 to the rear waist region 7 and provided with the hook element 21, and a third section 43 being contiguous to the second section 42 so as to extend from the rear waist region 7 to the front waist region 6. The first section 41 and the second section 42 are permanently bonded to each other in a second bonding zone 52 formed by appropriate adhesives or sealing techniques while the second section 42 and the third section 43 are permanently bonded to each other in a first bonding zone 51 formed by appropriate adhesives or sealing techniques. The supporting element 20 of such arrangement is destined to face and come in contact with the wearer's skin and, in consideration of this, nonwoven fabrics or woven fabrics providing a soft and comfortable feeding to wear are used as stock materials for the supporting element 20. Preferred types of nonwoven fabric include a spun bond nonwoven fabric, an air-through nonwoven fabric and a melt bond nonwoven fabric made of thermoplastic synthetic fibers having fineness in a range of 1 to 5 dtex and a basis weight in a range of 10 to 70 $g/m^2$. While it is not essential for such nonwoven fabrics to have a level of strength sufficient to function as sheet materials serving to connect the front and rear waist regions to each other, the respective sections 41, 42, 43 may be bonded one to another by means of the first bonding zone 51 and the second bonding zone 52 as shown to ensure the fastener means 14 to obtain a desired strength. For example, a stretching force in a circumferential direction P exerted on the supporting element 20 during use of the diaper 1 concentrate in a vicinity of an end 52a of the second bonding zone 52 encircled by an imaginary line A.

However, in the vicinity of the end 52a, the second section 42 and the third section 43 of the supporting element 20 are bonded together by means of the first bonding zone 51. Specifically two nonwoven fabric layers overlap here to enhance strength of the supporting element 20 and thereby to protect the supporting element 20 against being easily broken. In the vicinity of the end 52a, further more, the first section 41 of the supporting element 20 is bonded to the inner sheet 2 by means of an adhesive layer 24 and, in this section 41 also, the supporting element 20 is protected from being easily broken. The second section 42 of the supporting element 20 is bonded to the third section 43 by means of the first bonding zone 51 also in a vicinity of an end 21a of the hook element 21 encircled by an imaginary line B. Consequentially, it is unlikely that the supporting element 20 might be easily broken even when a stretching force in the circumferential direction P is exerted on a vicinity of the end 21a. The first and second bonding zones 51, 52 can be formed by locally sealing nonwoven fabrics made of thermoplastic synthetic fibers constituting the supporting element 20.

In the fastener means $14_L$ of FIG. 2, along a fold zone 46 connecting the first section 41 to the second section 42 and a fold zone 47 connecting the second section 42 to the third section 43 as well as in a gap zone 48 defined between an end 43a of the third section 43 and the second section 42, the respective sections of the supporting element 20 are not bonded one to another and separable one from another. In these zones 46, 47, 48, the nonwoven fabric layers placed one upon another and constituting the supporting element 20 are free to be independently and flexibly deformed. While the presence of the adhesive layer 24, the first bonding zone 51, the second bonding zone 52, the hook element 23 and vicinities thereof in the supporting element 20 tends to make the supporting element 20 stiff and to irritate the wearer's skin, the zones 46, 47, 48 function as cushioning zones to alleviate such undesirable irritation. In this way, there is no anxiety that the fastener means 14 attached to the inner side of the diaper 1 might irritate the wearer's skin. When it is not required for these zones 46, 47, 48 to function as the cushioning zones in the diaper, the respective sections of the supporting element 20 may be bonded one to another.

Figure 3:
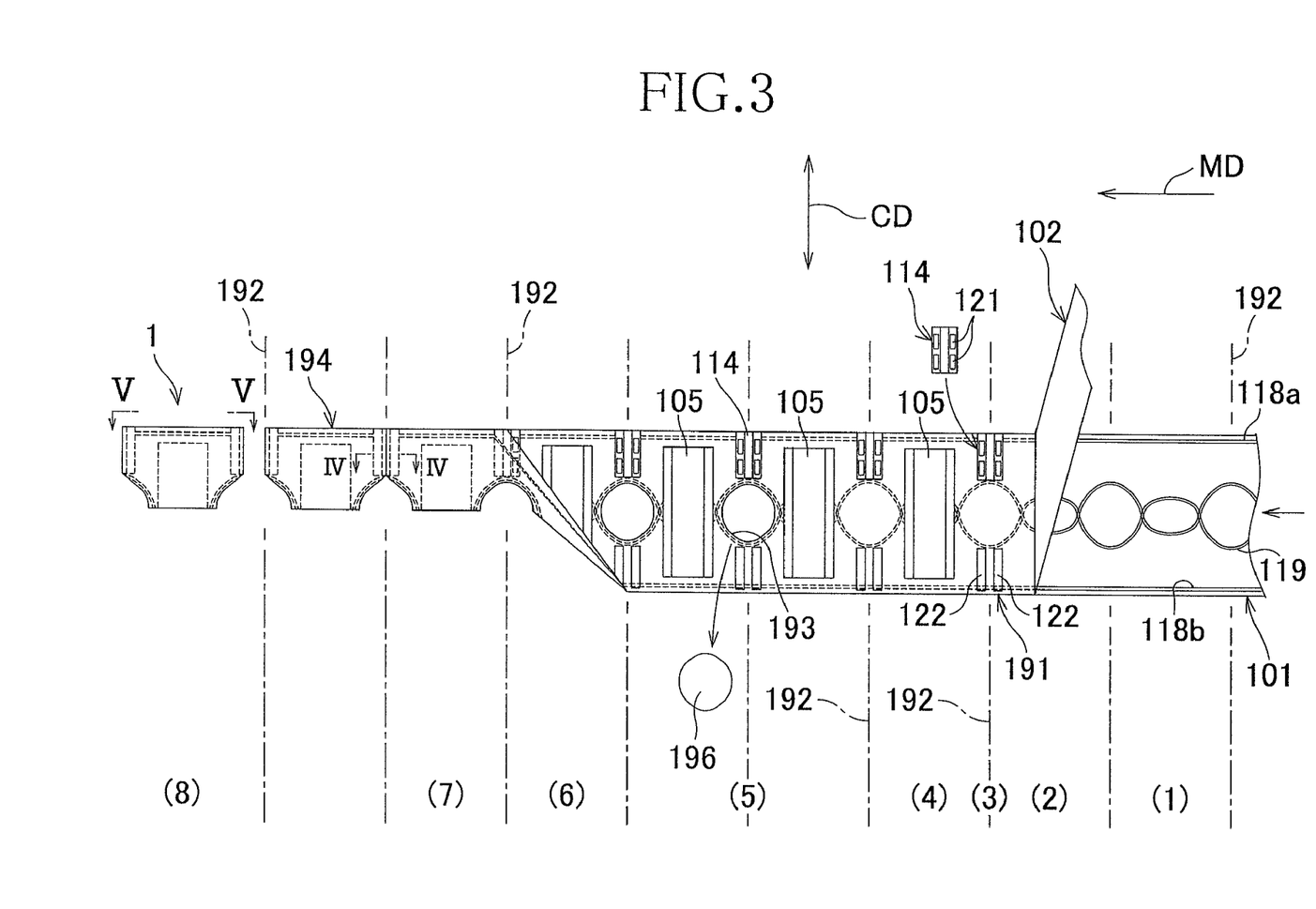
FIG. 3 is a diagram schematically illustrating the steps of a process for making the diaper.

FIG. 3 is a diagram schematically illustrating a part of a process for continuous production of the diaper 1 shown in FIG. 1, in which a direction from right to left is a machine direction MD. In a first step (1), a first web 101 corresponding to the continuous outer sheet 3 is fed from the right-hand side as viewed in FIG. 3. The first web 101 has first an elastic element 118a corresponding to the continuous front waist elastic element 18a, a second elastic element 118b corresponding to the continuous rear waist elastic element 18b and third elastic elements 119 corresponding to the continuous leg-surrounding elastic element 19 each previously attached in a stretched state to an inner surface of the first web 101.

In a second step (2), a second web 102 corresponding to the continuous inner sheet 2 is fed in the machine direction MD and bonded to the inner surface of the first web 101 to form a first composite web 191.

In a step (3), a composite fastener means 114 destined to become the fastener means 14 is bonded to a top surface of the second web 102 at a predetermined position on each cutting line 192 preset on the first composite web 191 to be cut in a later step (8) and a pair of loop elements 122 is bonded to the second web 102 at predetermined positions on both sides of the cutting line 192. The composite fastener means 114 includes a plurality of the hook elements 121. The pair of loop elements 122 may be replaced, if desired, by a single loop element crossing the preset cutting line 192.

In a step (4), a body fluid absorbent element 105 is bonded to the second web 102 at a predetermined position thereon.

In a step (5), the first composite web 191 is partially cut away immediately below the composite fastener means 114 as viewed in FIG. 3 and between each pair of the adjacent body fluid absorbent elements 105, 105 so as to form a circular opening 193 destined to define the leg-opening 17 of the diaper 1. Sheet strips cut away from the first composite web 191 are taken out from the line of the process.

In a step (6), the first composite web 191 is folded back along a center line (not shown) bisecting a width of this web 191 in a cross direction CD orthogonal to the machine direction MD with the second web 102 inside.

In a step (7), the hook element 121 included in the composite fastener means 114 bonded to the first composite web 191 is placed on and engaged with the loop element 122 bonded to the first composite web 191 to form a second composite web 194.

In a step (8), the second composite web 194 is cut along the preset cutting line 192 to obtain the individual diaper 1. The preset cutting line 192 extends in the cross direction CD along which the composite fastener means 114, the pair of loop elements 101 and the circular opening 193 are respectively bisected. In the course of the process from the step (1) to the step (8), an appropriate tension in the machine direction MD is exerted on the first and second webs 101, 102 as well as the first and second composite webs 191, 194 in order to ensure that two segments of the preset cutting line 192 exactly fall upon each other and the composite fastener means 114 exactly falls upon the associated loop element 122 when the first composite web 191 is folded back in the step (6). Particularly in the course from the step (5) to the step (7), the tension exerted on the first composite web 191 may be gradually increased to keep the hook element 121 and the associated loop element 122 on the composite fastener means 114 in close contact and engagement with each other. In this way, the individual diaper 1 can be reliably retained in a shape as shown by FIG. 5.

Figure 4:
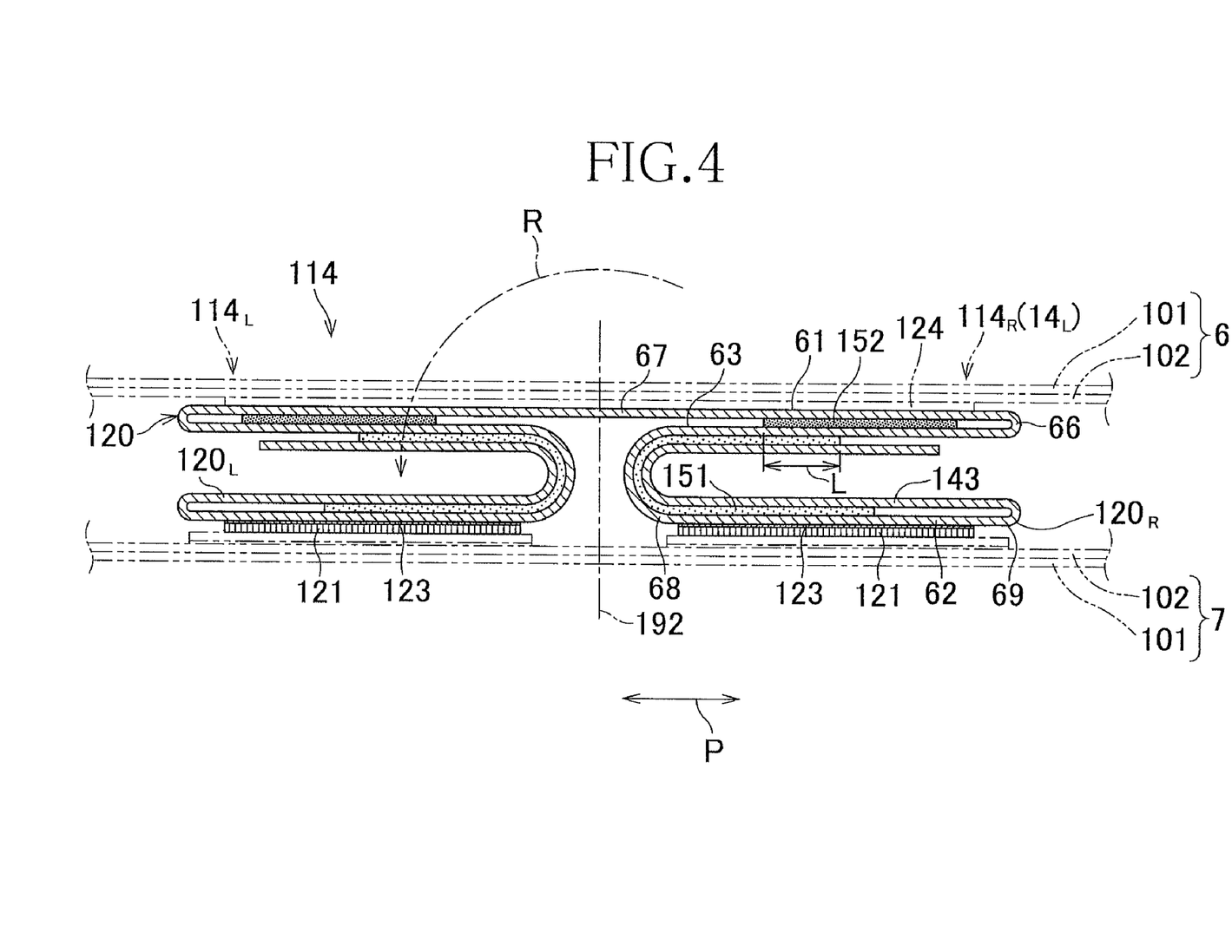
FIG. 4 is a sectional view taken along the line IV-IV in FIG. 3.

FIG. 4 is a sectional view taken along the line IV-IV in FIG. 3. It will be appreciated that only the composite fastener means 114 is indicated by solid lines and the other components such as the first and second webs 101, 102 as well as the loop element 122 are indicated by imaginary lines. It should be understood also that a dimension by which a bottom section 62 and an intermediate section 63 are spaced from each other is indicated in an exaggerated form. The composite fastener means 114 is symmetrically formed about the preset cutting line 192 and comprises a left half $114_L$ and a right half $114_R$ to be obtained after the composite fastener means 114 has been cut off along the preset cutting line 192. These left and right halves 114L, $114_R$ are respectively destined to form the right-hand side fastener means $14_R$ and the left-hand side fastener means $14_L$ of the individual diaper 1 (See FIG. 1). The composite fastener means 114 shown in FIG. 4 includes a composite supporting element 120 formed from a sheet-like material and a set of hook elements 121 (See FIG. 3) attached to the composite supporting element 120 by means of bonding means 123. Now this composite fastener means 114 will be described with respect to the right half $114_R$. In the right half $114_R$, a supporting element $120_R$ defined by one half of the composite supporting element 120 is folded in a Z-shape comprising a top section 61, a bottom section 62 and an intermediate section 63 connecting these top and bottom sections 61, 62. The top section 61 has a joint end 66 contiguous to the intermediate section 63 and an openable end 67 opposite to the joint end 66 and to be opened after the composite fastener means 114 has been cut off along the preset cutting line 192. The bottom section 62 has a joint end 68 contiguous to the intermediate section 63 and an openable end 69 opposite to the end 68. The top section 61 is bonded to the second web 102 by means of an adhesive layer 124. The bottom section 62 has the hook element 121 bonded thereto by means of bonding means 123. The supporting element $120_R$ is folded back along the openable end 69 of the bottom section 62 and extends along the bottom section 62 and the intermediate section 63 toward the joint end 66 of the top section 61 so as to be placed on these two sections 62, 63 and thereby to form a liner section 143. In the supporting element $120_R$ folded in this manner, opposed surfaces of these top section 61 and the intermediate section 63 are permanently bonded to each other in an upper bonding zone 152 having a length of at least 5 mm in the circumferential direction P. The bottom section 62 and the intermediate section 63 are respectively bonded to the liner section 143 in lower bonding zone 151 having a length in the circumferential direction P preferably smaller than the length of these two sections 62, 63. Having cut off the composite fastener means 114 along the preset cutting line 192, the first and second webs 101, 102 overlying the right half $114_R$ as viewed in FIG. 4 form the front waist region 6 of the individual diaper 1 shown in FIG. 1 while the first and second webs 101, 102 underlying the right half $114_R$ form the rear waist region 7 of the individual diaper 1 shown in FIG. 1 and the right half $114_R$ forms the left-hand side fastener means $14_L$ shown in FIG. 1. The left half $114_L$ in FIG. 4 includes a supporting element $120_L$ which is symmetrical to the right half $114_R$ and folded in an inverted Z-shape destined to be used as the right-hand side fastener means $14_R$ in the individual diaper 1. Specifically, this supporting element $120_L$ is destined to become the fastener means $14_L$ for the adjacent and preceding diaper 1 made by the process illustrated in FIG. 3 (See FIG. 5). In the diaper 1 obtained by the process as illustrated by FIGS. 3 and 4, the front and rear waist regions 6, 7 having the same width and placed upon each other. To form an annulus defined by the front and rear waist region as seen in FIG. 1 so that the diaper 1 can be put on the wearer's body, the top section 61 and the intermediate section 63 which is integral with the top section 61 may be unfolded in a direction indicated by an imaginary line R with the bottom section 62 held in a fixed state until the bottom section 62 and the intermediate section 63 are developed generally in a straight line from the supporting element $120_R$ folded in a Z-shape, for example, in the case of the right half $114_R$ in FIG. 4.

Figure 5:
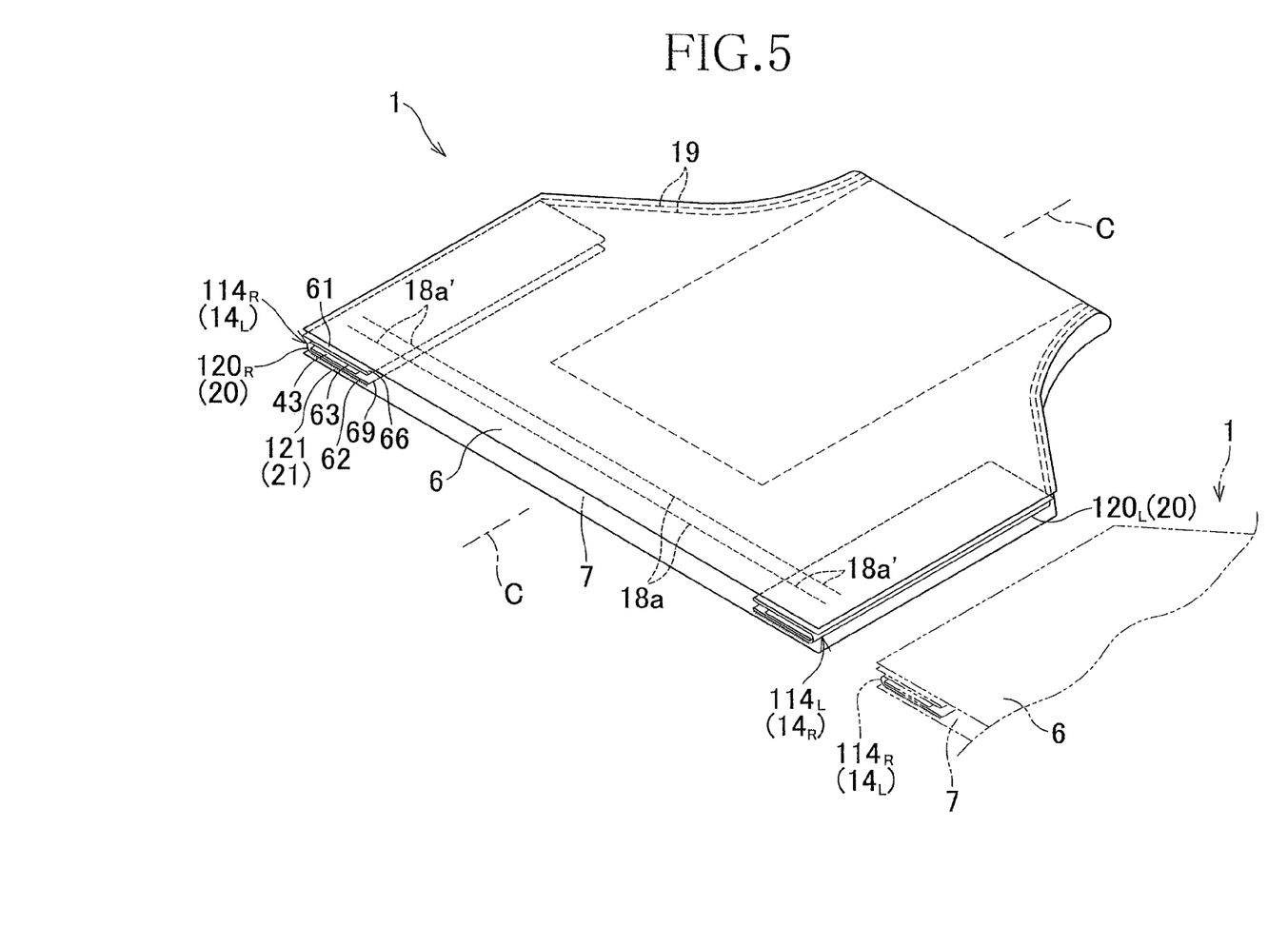
FIG. 5 is a perspective view of an individual diaper as viewed from the line V-V in FIG. 3.

FIG. 5 is a perspective view showing the individual diaper 1 as viewed from the line V-V in FIG. 3, showing also a center line C-C bisecting the width of the diaper 1. The diaper 1 partially shown by imaginary lines in FIG. 5 is the diaper 1 preceding the diaper 1 shown by solid lines. In the diaper 1, the waist-surrounding elastic elements 18a, 18b as well as the leg-surrounding elastic elements 19 are in a stretched state and the front and rear waist regions 6, 7 having the same width have been folded so as to be put flat together. The diaper 1 further includes the left half $114_L$ and the right half $114_R$ of the composite fastener means 114 as the fastener means $14_R$ and the fastener means $14_L$. The fastener means $14_L$ includes the supporting element 20 folded in a Z-shape. In this state, the respective sections of the supporting element 20 are designated just like the respective sections of the supporting element $120_R$ in FIG. 4. The front and rear waist regions 6, 7 of the diaper 1 put flat together may be separated from each other in a vertical direction as viewed in FIG. 5 to ensure that the top section 61 and the intermediate section 63 being integral with the top section 61 are unfolded and developed with respect to the bottom section 62 so as to describe a gentle circular arc or a generally straight line. In this way, the diaper 1 gets into the state as seen in FIGS. 1 and 2. Specifically, the right half $114_R$ in FIG. 4 corresponding to the fastener means $14_L$ in FIG. 5 corresponds to the fastener means $14_L$ in FIG. 2. Accordingly, the respective sections of the right half $114_R$ correspond to the respective sections of the fastener means $14_L$ in FIG. 2 in a relationship as follows: The supporting element $120_R$ and the hook element 121 in the right half $114_R$ shown in FIG. 4 respectively correspond to the supporting element $20_R$ and the hook element 21 in FIG. 2. The top section 61 of the supporting element $120_R$ in FIG. 4 corresponds to the first section 41 in FIG. 2; the bottom section 62 and the intermediate section 63 in FIG. 4 respectively correspond to the second section 42 in FIG. 2; the liner section 143 in FIG. 4 corresponds to the third section 43 in FIG. 2; the upper bonding zone 152 and the lower bonding zone 151 in FIG. 4 respectively correspond to the second bonding zone 52 and the first bonding zone 51 in FIG. 2; and the joint end 66 of the top section and the openable end 69 of the bottom section in FIG. 4 respectively correspond to the fold zone 46 and the fold zone 47 in FIG. 2. In a height direction of the right half $114_R$ in FIG. 4, the upper bonding zone 152 and the lower bonding zone 151 are placed upon each other with interposition of the liner section 143. A dimension L in the circumferential direction P by which these upper bonding zone 152 and lower bonding zone 151 overlap each other each other is preferably at least about 3 mm. In the preferred diaper 1, the portions of the waist-surrounding elastic elements 18a, 18b and the leg-surrounding elastic elements 19 extending on the fastener means 14 and the loop element 22 may be subjected to an appropriate treatment to prevent the fastener means 14 and the loop element 22 from being formed with gathers under contraction of these elastic elements 18a, 18b, 19. Referring to FIG. 5, for example, the portion 18a' of the front waist elastic element 18a extending on the fastener means $14_L$, $14_R$ may be attached in a non-stretched state to the front waist region 6 or attached in a non-contractible state to the front waist region 6.

The process schematically illustrated in FIG. 3 advantageously simplifies operation of attaching the fastener means 14 to the diaper 1 along the side edges and thereby facilitate the pants-type diaper 1 to be continuously produced by using the fastener means $14_L$, $14_R$ forming the fastener means 14 and the halves $114_L$, $114_R$ forming the composite fastener means 114 as have been described above. It should be noted here that the diaper 1 can be produced by various modifications of the process schematically illustrated in FIG. 3. For example, the sequence of the steps (3), (4) and (5) may be appropriately interchanged. It is possible to attach the composite fastener means 114 to the rear waist region 7 rather than to the front waist region 6. It is also possible to bring the loop element 122 in engagement with the hook element 121 of the composite fastener means 114 rather than attaching the loop element 122 to the second web 102 in the step (3) and to attach the loop element 122 to the second web 102 facing the loop element 122 after the first composite web 191 has been folded back in the step (6).

Figure 6:
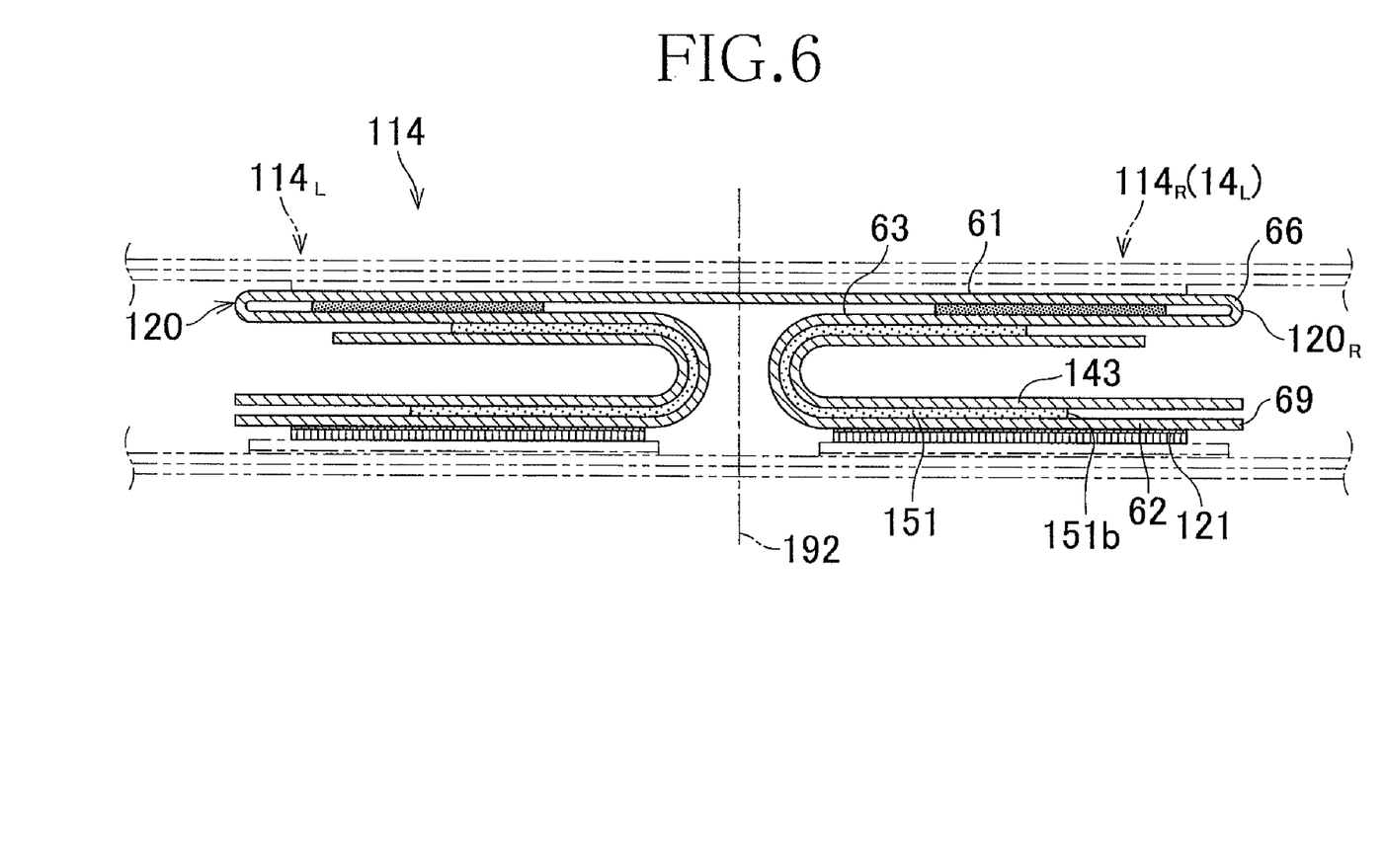
FIG. 6 is a view similar to FIG. 4, showing an embodiment of combined fastener means.

FIG. 6 is a view similar to FIG. 4, showing an embodiment of the combined fastener means 114. In the composite fastener means 114 according to this embodiment, the liner section 143 is formed from a sheet material provided separately from a series of the top section 61, the intermediate section 63 and the bottom section 62. The liner section 143 extending from a vicinity of the bottom section's openable end 69 toward the top section's joint end 66 is not connected to the bottom section's openable end 69 but extends outward in a horizontal direction from the end zone 151b of the first bonding zone 151. The liner section 143 included in the fastener means $14_L$ obtained from the right half $114_R$ of this composite fastener means 114 functions in the similar manner as the second section 43 in FIG. 2. Specifically, the liner section 143 improves a tensile strength of the fastener means $14_L$ and simultaneously prevents the end zone 151b of the first bonding zone 151 corresponding to the upper bonding zone 51 as well as the end zone of the hook element 121 from coming in direct contact with the wearer's skin. In other words, the liner section 143 functions as a cushioning material adapted to alleviate an undesirable irritating effect to the wearer's skin. While particular types of the sheet material to be used for the liner section 143 is not specified, if nonwoven fabrics forming the composite supporting element 120 has a poor sweat-absorbency, the sheet material of high sweat-absorbency may be used for the liner section 143 to protect the wearer from getting heat rash even if the fastener means 14 comes in close contact with the wearer's skin during use of the diaper 1.

Figure 7:
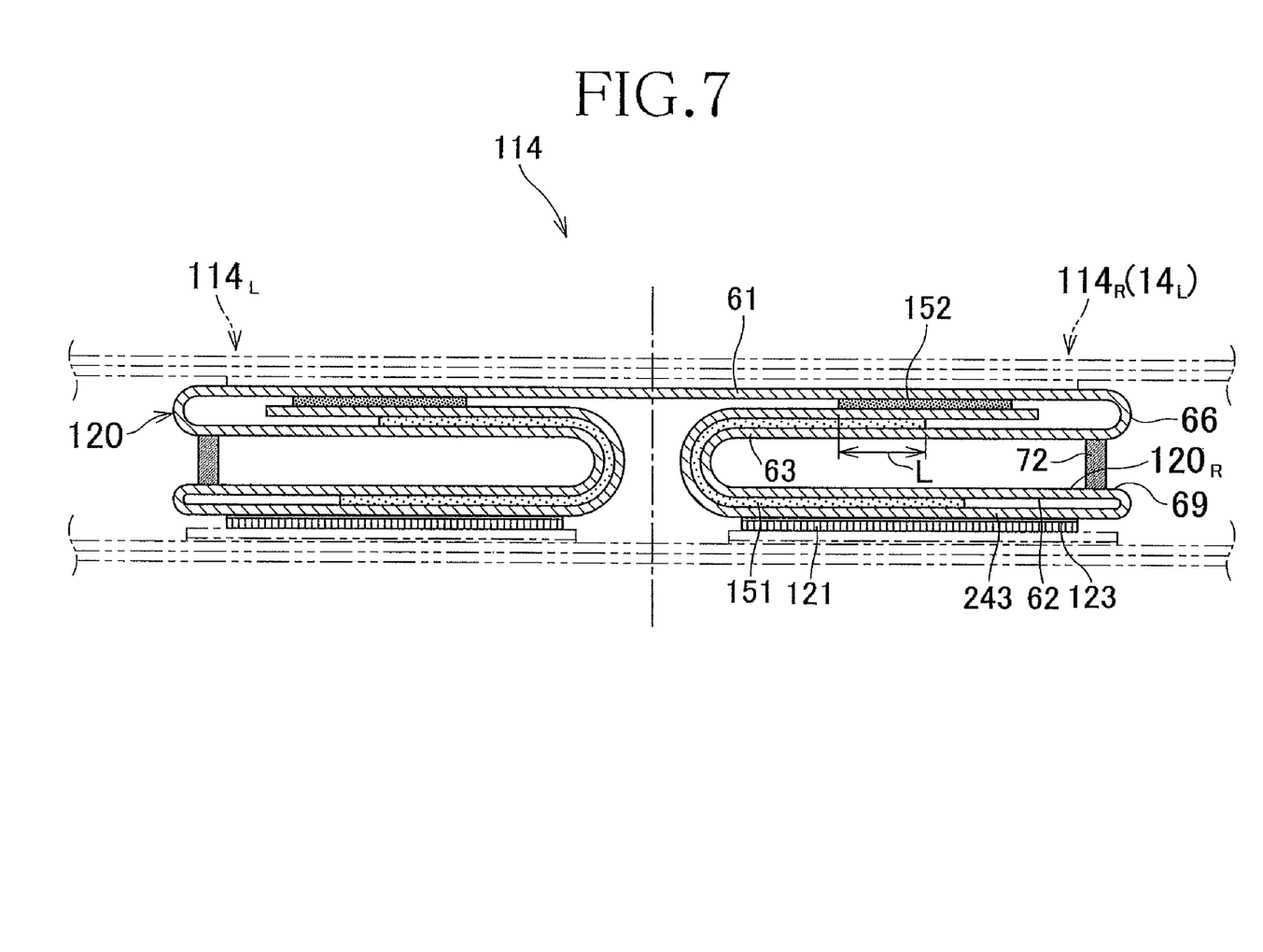
FIG. 7 is a view similar to FIG. 4, showing another embodiment of combined fastener means.

FIG. 7 also is a view similar to FIG. 4, showing another embodiment of combined fastener means 114. In the right half $114_R$ of this composite fastener means 114, the supporting element $120_R$ as a constituent element thereof is folded downward in a vicinity of the bottom section's openable end 69 so as to extend toward the top section's joint end 66 and has a lapping section 243 adapted to lap the bottom section 62 and the intermediate section 63 in a manner as shown. The lapping section 243 is bonded to the top section 61 in the upper bonding zone 152 and bonded to the bottom section 62 as well as to the intermediate section 63 in the lower bonding zone 151. The lower bonding zone 151 and the upper bonding zone 152 overlap each other by a dimension L and this dimension L in the right half $114_R$ is preferably at least 3 mm. The hook element 121 is attached to the lapping section 243 by means of the bonding means 123. The bottom section 62 and the intermediate section 63 are detachably bonded by means of temporary bonding means 72 such as a pressure-sensitive adhesive or temporary sealing. The temporary bonding means 72 is provided for the purpose of merely retaining the shape of the supporting element $120_R$ folded in a Z-shape in the course of process for producing the diaper 1 and has a bonding strength at a degree such that the bottom section 62 and the intermediate section 63 may be easily separated when it is desired to put the diaper 1 on the wearer's body. The fastener means $14_L$ obtained from the right half $114_R$ of such arrangement provides a functional effect similar to that provided by the fastener means $14_L$ in FIG. 4. More specifically, the supporting element $120_R$ is capable of functioning as the cushioning material in the fastener means $14_L$ and the lapping section 243 provides a reinforcing effect for the bottom section 62 as well as for the intermediate section 63 just like the liner section 143 although the lapping section 243 is bonded to the bottom section 62 and the intermediate section 63 in a manner differing from the manner in which the liner section 143 of FIG. 4 is bonded to these sections. While the hook element 121 is bonded to the lapping section 243, this lapping section 243 is integrated with the bottom section 62 by means of the lower bonding zone 151 and thus substantially bonded to the bottom section 62. While FIG. 7 shows the embodiment in which the top section 61 is bonded to the lapping section 243 by means of the upper bonding zone 152, such embodiment may be replaced by still another embodiment in which the top section 61 is bonded to the lapping section 243 and the intermediate section 63.

To exploit the present invention, the hook element 21 employed in the illustrated embodiment may be replaced by the loop element or pressure-sensitive adhesive. Furthermore, the loop element 22 cooperating with the hook element 21 may be replaced by the hook element or landing surface cooperating with the pressure-sensitive adhesive. In the case of embodiment wherein the hook element 21 and the inner sheet 2 are adapted to be repetitively engaged with and disengaged from each other, the loop element 22 may be replaced by the inner sheet 2 as a component cooperating with the hook element 21. Dimension of the fastener means 14 in the diaper 1 in the longitudinal direction as well as in the transverse direction is not specified and, for example, the longitudinal dimension may be adjusted to be the same as or shorter than the length of the side edge length of the front and rear waist regions. While the hook element 21 is illustrated to be divided in two in the vertical direction, the hook element 21 may be divided in three or used in a serial form not divided at all. It is also possible to attach the fastener means 14 attached to the rear waist region 7 rather than to the front waist region 6 as in the illustrated embodiment. The present invention having been described hereinabove on the basis of the disposable diaper 1 is applicable also to various pants such as training pants or pants for incontinent patient. While the bottom section's openable end 69 of the supporting element $120_R$ is really contiguous to the liner section 143 in FIG. 4, this end zone 69 can be cut off from the liner section 143 as seen in FIG. 6. It is for this reason that this end zone is referred to as "openable end 69".

The present invention makes it possible to produce the wearing article including the fastener means improved to be not easily broken.

What is claimed is:

1. A pants-type wearing article, comprising:
   a first waist region corresponding to one of front and rear waist regions;
   a second waist region corresponding to the other of said front and rear waist regions;
   fastener members fastening said first and second waist regions together in a detachable and refastenable manner along transversely opposite edges of the waist regions so that,
   in a state where said first and second waist regions are put flat together, said fastener members respectively have, as viewed in a circumferential direction of the wearing article, a Z-shape and an inverted Z-shape being symmetrical to each other about a center line bisecting a width of said first and second waist regions;
   wherein each said fastener member includes
      a supporting element folded in said Z-shape or said inverted Z-shape, and
      a fastener element attached to said supporting element,
   wherein said supporting element in the circumferential direction has a top section, a bottom section extending in parallel to the top section, and an intermediate section extending between said top section and said bottom section,
   wherein
   said top section has a top section's joint end being contiguous to said intermediate section and a top section's openable end opposed to said joint end,
   said bottom section has a bottom section's joint end being contiguous to said intermediate section and a bottom section's openable end opposed to said joint end, and
   said top section is permanently attached to an inner surface of said first waist region while said bottom section is attached to said second waist region by said fastener member in a detachable and refastenable manner;
   said supporting element further has a liner section extending from a vicinity of said bottom section's openable end along said bottom section and said intermediate section toward said top section's joint end and covering said bottom section and said intermediate section;

said liner section is directly bonded to said bottom section and said intermediate section in a first bonding zone extending between said bottom section's openable end and said top section's joint end;

said top section is bonded to one of (i) said intermediate section and (ii) said liner section in said intermediate section in a second bonding zone; and in a height direction of said Z-shape and said inverted Z-shape, said first bonding zone and said second bonding zone overlap each other.

2. The article according to claim 1, wherein said first bonding zone and said second bonding zone overlap each other between said top section's joint end and said bottom section's joint end by a dimension of at least 3 mm.

3. The article according to claim 1, wherein said fastener member is a pressure-sensitive adhesive.

4. The article according to claim 1, wherein said supporting element is formed from a nonwoven fabric made of thermoplastic synthetic fibers having a fineness in a range of 1 to 5 dtex and having a basis weight in a range of 10 to 70 g/m$^2$.

5. The article according to claim 1, wherein said top section and one of said intermediate section and said liner section in said intermediate section are free of said second bonding zone in a vicinity of said top section's joint end and are spaced from each other.

6. The article according to claim 1, wherein said bottom section and said liner section are free of said first bonding zone in the vicinity of said bottom section's openable end and are spaced from each other.

7. The article according to claim 1, wherein said liner section is formed by folding back said supporting element in a vicinity of said bottom section's openable end.

8. The article according to claim 1, wherein said liner section is formed from a sheet material provided separately of said supporting element and said liner section is directly bonded to the intermediate section at the first bonding zone.

9. The article according to claim 1, wherein one of said first bonding zone and said second bonding zone is formed by heat sealing thermoplastic synthetic fibers contained in said supporting element and said liner section.

10. The article according to claim 1, wherein the liner section is folded along the intermediate section between the bottom section's openable end and the top section's joint end.

11. The article according to claim 1, wherein the top section is permanently bonded to an inner surface of the first waist region by an adhesive layer, and the bottom section is bonded to a hook element attached to each of the transversely opposite edges of the second waist region.

12. The article according to claim 1, wherein the top section is permanently bonded to the intermediate section in the second bonding zone having a length of at least 5 mm in the circumferential direction.

13. The article according to claim 8, wherein said liner section extending from a vicinity of the bottom section's openable end toward the top section's joint end is free of direct connection to the bottom section's openable end and extends outwardly from an end zone of the first bonding zone.

14. The article according to claim 1, wherein the bottom section and the intermediate section are respectively bonded to the liner section in the first bonding zone having a length in the circumferential direction smaller than a length of the bottom and intermediate sections.

15. The article according to claim 1, wherein said supporting element is folded downward in a vicinity of the bottom section's openable end and extends toward the top section's joint end, said supporting element has a lapping section adapted to lap the bottom section and the intermediate section.

16. The article according to claim 15, wherein said lapping section is directly bonded to the top section in the second bonding zone and directly bonded to the bottom section as well as to the intermediate section in the first bonding zone.

17. The article according to claim 16, wherein said first bonding zone and the second bonding zone overlap each other by a dimension of at least 3 mm.

18. The article according to claim 17, wherein said bottom section and the intermediate section are detachably bonded by a temporary bonding element where the top section is spaced from the intermediate section in a vicinity of the top section's joint end and the bottom section is spaced from the lapping section in a vicinity of the bottom section's openable end.

19. The article according to claim 1, wherein said fastener member is selected from the group consisting of (i) a hook element constituting a mechanical fastener, wherein said mechanical fastener further includes a loop element detachably engageable with the hook element, and (ii) a loop element constituting a mechanical fastener, wherein said mechanical fastener further includes a hook element detachably engageable with the loop element.

* * * * *